United States Patent
Huang et al.

(10) Patent No.: US 12,354,763 B2
(45) Date of Patent: Jul. 8, 2025

(54) BEAM IRRADIATION SYSTEM AND CONTROL METHOD THEREOF

(71) Applicant: NEUBORON THERAPY SYSTEM LTD., Fujian (CN)

(72) Inventors: Yongyin Huang, Fujian (CN); Weilin Chen, Fujian (CN)

(73) Assignee: NEUBORON THERAPY SYSTEM LTD., Fujian (CN)

( * ) Notice: Subject to any disclaimer, the term of this patent is extended or adjusted under 35 U.S.C. 154(b) by 382 days.

(21) Appl. No.: 17/734,190

(22) Filed: May 2, 2022

(65) Prior Publication Data

US 2022/0262536 A1    Aug. 18, 2022

Related U.S. Application Data

(63) Continuation of application No. PCT/CN2020/125767, filed on Nov. 2, 2020.

(30) Foreign Application Priority Data

Nov. 7, 2019    (CN) .......................... 201911083860.5

(51) Int. Cl.
*G21K 5/04* (2006.01)
*A61N 5/10* (2006.01)
*G21K 5/10* (2006.01)

(52) U.S. Cl.
CPC ............. *G21K 5/04* (2013.01); *A61N 5/1048* (2013.01); *A61N 5/1079* (2013.01); *G21K 5/10* (2013.01);
(Continued)

(58) Field of Classification Search
CPC .......... G21K 5/04; G21K 5/10; A61N 5/1048; A61N 5/1079; A61N 2005/1087;
(Continued)

(56) References Cited

U.S. PATENT DOCUMENTS

2007/0176125 A1*  8/2007  Natori ...................... A61N 5/10
                                                            250/493.1
2012/0119115 A1*  5/2012  Iwata ....................... G21K 5/00
                                                            600/529
(Continued)

FOREIGN PATENT DOCUMENTS

CN    104780974 A    7/2015
CN    105792890 A    7/2016
(Continued)

OTHER PUBLICATIONS

International Search Report of PCT/CN2020/125767, Jan. 27, 2021.

*Primary Examiner* — David E Smith
*Assistant Examiner* — Christopher J Gassen
(74) *Attorney, Agent, or Firm* — Troutman Pepper Locke LLP; Tim Tingkang Xia, Esq.

(57) ABSTRACT

Provided is a beam irradiation system and a control method thereof. The beam irradiation system includes: a first irradiation chamber and a second irradiation chamber; a beam generation device to generate a beam and emit the beam to the first or second irradiation chambers; a system control module including a first control sub-module capable of controlling the beam generation device to emit the beam to the first irradiation chamber, and a second control sub-module capable of controlling the beam generation device to emit the beam to the second irradiation chamber; and a beam control module connected between the beam generation device and the system control module. For the first and second control sub-modules, one is capable of controlling the beam generation device through the beam control module when the beam control module is not occupied by the other, such that the same beam irradiation system controls multiple irradiation chambers respectively.

18 Claims, 5 Drawing Sheets

(52) U.S. Cl.
CPC  *A61N 2005/1087* (2013.01); *A61N 2005/109* (2013.01)

(58) Field of Classification Search
CPC ...... A61N 2005/109; A61N 2005/1094; A61N 5/1077; A61N 5/1065
See application file for complete search history.

(56) References Cited

U.S. PATENT DOCUMENTS

| | | |
|---|---|---|
| 2015/0328482 A1 | 11/2015 | Hishikawa |
| 2016/0279446 A1* | 9/2016 | Tachibana ............ A61N 5/1081 |
| 2016/0346567 A1 | 12/2016 | Ishiguro et al. |
| 2017/0203125 A1 | 7/2017 | Amato et al. |
| 2017/0301508 A1 | 10/2017 | Ma et al. |
| 2018/0168727 A1 | 6/2018 | Lin et al. |

FOREIGN PATENT DOCUMENTS

| | | |
|---|---|---|
| CN | 107092571 A | 8/2017 |
| CN | 107441626 A | 12/2017 |
| CN | 108379750 A | 8/2018 |
| CN | 109464750 A | 3/2019 |
| CN | 110159442 A | 8/2019 |
| CN | 209451161 U | 10/2019 |
| JP | 2006034701 A | 2/2006 |
| JP | 2007105256 A | 4/2007 |
| TW | 201820055 A | 6/2018 |
| TW | 201830149 A | 8/2018 |
| TW | 201839793 A | 11/2018 |
| WO | 2011009742 A1 | 1/2011 |
| WO | 2015075797 A1 | 3/2017 |
| WO | 2018006550 A1 | 1/2018 |

\* cited by examiner

BEAM IRRADIATION SYSTEM AND CONTROL METHOD THEREOF

CROSS-REFERENCE TO RELATED PATENT APPLICATION

This application is a continuation application of International Application No. PCT/CN2020/125767, filed on Nov. 2, 2020, which claims priority to Chinese Patent Application No. 201911083860.5, filed on Nov. 7, 2019, the disclosures of which are hereby incorporated by reference.

FIELD

The present disclosure relates to the technical field of beam irradiation, and more particularly, to a beam irradiation system and a control method thereof.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Conventional beam irradiation systems, most of which use the same control module to control a single or multiple irradiation chambers, have been widely used in the field of beam irradiation because of their simplicity and ease of operation.

However, since the hardware and software of the control module of the beam irradiation system are relatively single, the irradiation against the irradiation chamber cannot be performed once the control module is in an overhaul state or when a software or hardware damage occurs, such that the beam irradiation system cannot be fully utilized.

SUMMARY

In order to solve the above-mentioned technical problem, an embodiment of the present disclosure provides a beam irradiation system and a control method thereof, such that a plurality of control sub-modules in the same beam irradiation system respectively control a plurality of irradiation chambers, thereby avoiding that the irradiation cannot be performed when a single control module is in an overhaul state or when a software or hardware damage occurs.

In a first aspect of an embodiment of the present disclosure, an embodiment of the present disclosure provides a beam irradiation system. The system includes: a first irradiation chamber and a second irradiation chamber; a beam generation device configured to generate a beam and emit the beam to the first irradiation chamber or the second irradiation chamber; a system control module including a first control sub-module and a second control sub-module, wherein the first control sub-module corresponds to the first irradiation chamber and is capable of controlling the beam generation device to emit the beam to the first irradiation chamber, and the second control sub-module corresponds to the second irradiation chamber and is capable of controlling the beam generation device to emit the beam to the second irradiation chamber; and a beam control module connected between the beam generation device and the system control module, one of the first control sub-module and the second control sub-module being capable of controlling the beam generation device through the beam control module when the beam control module is not occupied by the other of the first control sub-module and the second control sub-module.

In an embodiment of the present disclosure, the beam control module is capable of obtaining data of the beam generation device and performing data interaction with the system control module, and the beam generation device is connected to and performs data interaction with the system control module.

In an embodiment of the present disclosure, the first irradiation chamber and the second irradiation chamber are provided with an irradiated body supporting assembly and an irradiation radiation monitoring assembly, and the system control module is capable of receiving data of the irradiated body supporting assembly and the irradiation radiation monitoring assembly and controlling a movement of the irradiated body supporting assembly.

In an embodiment of the present disclosure, the system control module further includes a data interconnection and sharing module, the first control sub-module and the second control sub-module are respectively connected to and perform data interaction with the data interconnection and sharing module, the first control sub-module and the second control sub-module are further configured to store irradiation data of the first irradiation chamber and the second irradiation chamber, respectively, and the data interconnection and sharing module is configured to share the irradiation data of the first irradiation chamber and the second irradiation chamber between the first control sub-module and the second control sub-module.

In an embodiment of the present disclosure, the beam control module is connected to the system control module through the data interconnection and sharing module, the beam control module performs data interaction with the data interconnection and sharing module, the first irradiation chamber and the second irradiation chamber are connected to and perform data interaction with the data interconnection and sharing module, and the first control sub-module and the second control sub-module control the beam control module, the first irradiation chamber and the second irradiation chamber through the data interconnection and sharing module.

In an embodiment of the present disclosure, the beam generation apparatus includes a charged particle generation portion, a beam transmission portion, a first neutron generation portion and a second neutron generation portion, the beam control module being capable of controlling the charged particle generation portion to generate charged particles and capable of controlling the beam transmission portion to selectively transmit the charged particles generated by the charged particle generation portion to the first neutron beam generation portion or the second neutron beam generation portion, a neutron beam generated by the first neutron beam generation portion being irradiated to the first irradiation chamber, and a neutron beam generated by the second neutron beam generation portion being irradiated to the second irradiation chamber.

In an embodiment of the present disclosure, the charged particle generation portion includes an accelerator, an accelerator radiation monitoring assembly and an accelerator auxiliary device, the beam control module being capable of receiving data information of the accelerator, the accelerator radiation monitoring assembly and the accelerator auxiliary device and controlling the accelerator to generate charged particles.

In a second aspect of the embodiment of the present disclosure, an embodiment of the present disclosure provides a control method for a beam irradiation system. The method includes: receiving, by a first control sub-module, an instruction indicating irradiation of a first irradiation chamber, which is input by a user; obtaining, by the first control sub-module, a control right of a beam control module according to the instruction indicating irradiation of the first irradiation chamber when the control right of the beam control module is in a released state, so as to control, through the beam control module, the beam generation device to emit a beam to the first irradiation chamber; waiting, by the first control sub-module, for a release of the control right of the beam control module, when the control right of the beam control module is in a state of being occupied by the second control sub-module; receiving, by the first control sub-module, an instruction indicating stopping irradiation of the first irradiation chamber, which is input by the user; and releasing, by the first control sub-module, the control right of the beam control module according to the instruction indicating stopping irradiation of the first irradiation chamber.

In an embodiment of the present disclosure, before receiving, by the first control sub-module, the instruction indicating irradiation of the first irradiation chamber, which is input by the user, or when the control right of the beam control module is in the state of being occupied by the second control sub-module, the control method further includes: receiving, by the first control sub-module, an instruction indicating preparation for the first irradiation chamber, which is input by the user; and controlling, by the first control sub-module, the first irradiation chamber to complete a preparatory work before irradiation according to the instruction indicating preparation for the first irradiation chamber.

In an embodiment of the present disclosure, the system control module further comprises a data interconnection and sharing module, wherein the data interconnection and sharing module is connected to the first control sub-module and the second control sub-module, and the first control sub-module and the second control sub-module are connected to the beam control module through the data interconnection and sharing module, respectively, and the control method further includes: receiving, by the first control sub-module, a determination result of determining, by the data interconnection and sharing module, that the control right of the beam control module is in a released state or an occupied state; and determining, by the first control sub-module according to the determination result, whether the control right of the beam control module is to be obtained.

In a third aspect of an embodiment of the present disclosure, an embodiment of the present disclosure provides a beam irradiation system. The system includes: a first irradiation chamber and a second irradiation chamber; a beam generation device configured to generate a beam and emit the beam to the first irradiation chamber or the second irradiation chamber; and a system control module including a first control sub-module, a second control sub-module and a data interconnection and sharing module, wherein the first control sub-module corresponds to the first irradiation chamber and is capable of controlling the beam generation device to emit the beam to the first irradiation chamber, the second control sub-module corresponds to the second irradiation chamber and is capable of controlling the beam generation device to emit the beam to the second irradiation chamber, the first control sub-module and the second control sub-module are configured to store irradiation data of the first irradiation chamber and the second irradiation chamber, respectively, and the data interconnection and sharing module is configured to share the irradiation data of the first irradiation chamber and the second irradiation chamber between the first control sub-module and the second control sub-module.

In an embodiment of the present disclosure, the beam irradiation system further includes a beam control module connected between the beam generation device and the system control module, one of the first control sub-module and the second control sub-module being capable of controlling the beam generation device through the beam control module when the beam control module is not occupied by the other of the first control sub-module and the second control sub-module.

In an embodiment of the present disclosure, the beam generation device is connected to and performs data interaction with the system control module; the beam control module is capable of obtaining data of the beam generation device and is connected to the system control module through the data interconnection and sharing module; the beam control module performs data interaction with the data interconnection and sharing module; the first irradiation chamber, the second irradiation chamber, the first control sub-module and the second control sub-module are connected to and perform data interaction with the data interconnection and sharing module, respectively; and the first control sub-module and the second control sub-module control the beam control module, the first irradiation chamber and the second irradiation chamber through the data interconnection and sharing module.

In an embodiment of the present disclosure, the first irradiation chamber and the second irradiation chamber are provided with an irradiated body supporting assembly and an irradiation radiation monitoring assembly, and the system control module is capable of receiving data of the irradiated body supporting assembly and the irradiation radiation monitoring assembly and controlling a movement of the irradiated body supporting assembly.

In an embodiment of the present disclosure, the beam generation device includes a charged particle generation portion, a beam transmission portion, a first neutron generation portion and a second neutron generation portion, the beam control module being capable of controlling the charged particle generation portion to generate charged particles and capable of controlling the beam transmission portion to selectively transmit the charged particles generated by the charged particle generation portion to the first neutron beam generation portion or the second neutron beam generation portion, a neutron beam generated by the first neutron beam generation portion being irradiated to the first irradiation chamber, and a neutron beam generated by the second neutron beam generation portion being irradiated to the second irradiation chamber; the charged particle generation portion comprises an accelerator, an accelerator radiation monitoring assembly and an accelerator auxiliary device, the beam control module being capable of receiving data information of the accelerator, the accelerator radiation monitoring assembly and the accelerator auxiliary device and controlling the accelerator to generate charged particles.

According to the technical solutions described in the embodiments of the present disclosure, a first control sub-module and a second control sub-module are provided in the system control module, the first control sub-module and the second control sub-module respectively control the first irradiation chamber and the second irradiation chamber correspondingly, and any control sub-module of the multiple control sub-modules controls the beam generation device to emit a beam to the corresponding irradiation chamber, thereby realizing that the multiple control sub-modules in the same beam irradiation system respectively control the multiple irradiation chambers, and avoiding that the irradiation cannot be performed when a single control module is in an overhaul state or when a software or hardware damage occurs.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The accompanying drawings illustrate one or more embodiments of the disclosure and together with the written description, serve to explain the principles of the disclosure. Wherever possible, the same reference numbers are used throughout the drawings to refer to the same or like elements of an embodiment.

DETAILED DESCRIPTION OF THE DISCLOSURE

The technical solutions of the embodiments of the present disclosure are clearly and comprehensively described in connection with the accompanying drawings, which are intended to be used in connection with the embodiments of the present disclosure. It is apparent that the accompanying drawings described below illustrate only a part, but not all, of the embodiments of the present disclosure.

It is to be noted that, based on the embodiments of the present disclosure, all related embodiments obtained by a person skilled in the art without involving any inventive effort are within the scope of the present disclosure.

An embodiment of the present disclosure provides a beam irradiation system and a control method thereof, which are described in detail below.

Figure 1:
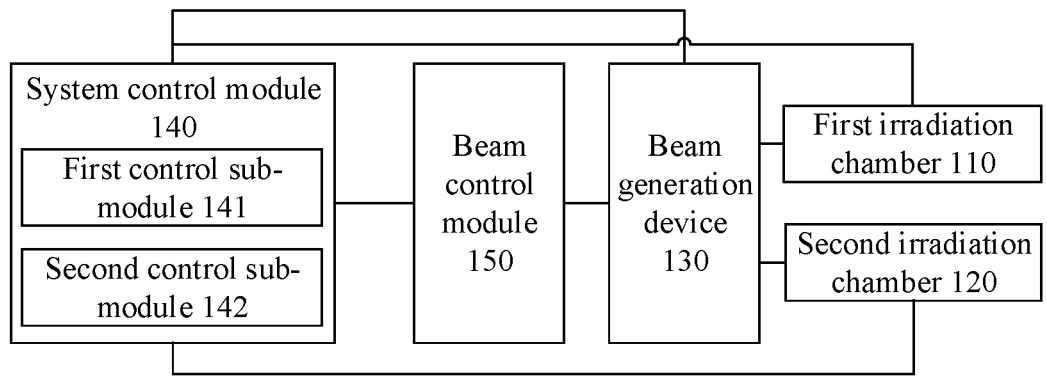
FIG. 1 is a block diagram of a beam irradiation system according to an embodiment of the present disclosure.

FIG. 1 is a block diagram of a beam irradiation system according to an embodiment of the present disclosure. As shown in FIG. 1, the beam irradiation system 100 includes a first irradiation chamber 110, a second irradiation chamber 120, a beam generation device 130, a system control module 140, and a beam control module 150.

The beam generation device 130 is configured to generate a beam and emit the beam to the first irradiation chamber 110 or the second irradiation chamber 120. The system control module 140 includes a first control sub-module 141 corresponding to the first irradiation chamber 110 and capable of controlling the beam generation device 130 to emit a beam to the first irradiation chamber 110, and a second control sub-module 142 corresponding to the second irradiation chamber 120 and capable of controlling the beam generation device 130 to emit a beam to the second irradiation chamber 120. The beam control module 150 is connected between the beam generation device 130 and the system control module 140, and one of the first control sub-module 141 and the second control sub-module 142 is capable of controlling the beam generation device 130 through the beam control module 150 when the beam control module 150 is not occupied by the other of the first control sub-module 141 and the second control sub-module 142.

According to the technical solution provided in the embodiment of the present disclosure, a first control sub-module and a second control sub-module are provided in the system control module, the first control sub-module and the second control sub-module respectively control the first irradiation chamber and the second irradiation chamber correspondingly, and any control sub-module of the multiple control sub-modules controls a beam generation device to emit a beam to the corresponding irradiation chamber through the beam control module, such that the first control sub-module in the system control module controls the first irradiation chamber, and the second control sub-module controls the second irradiation chamber. When the first control sub-module is in an overhaul state or when a software or hardware damage occurs, the second control sub-module may be used to control the second irradiation chamber, thereby overcoming the difficulty of irradiation when a single control module is in the overhaul state or when a software or hardware damage occurs, which would affect the normal operation. Meanwhile, the control sub-modules are provided in one-to-one correspondence with the irradiation chambers to avoid misoperation, and any one of the control sub-modules can only control the corresponding irradiation chamber, and cannot control the other irradiation chambers in any case, thereby avoiding accidental emission of a beam to the irradiation chamber which need not be irradiated, and increasing the safety and reliability of system operation. It is to be understood that each control sub-module may further control the other irradiation chambers at the same time. In addition, a beam control module and a beam generation device are shared by multiple control sub-modules such as the first control sub-module and the second control sub-module, thereby reducing the cost of the beam irradiation system.

It is to be understood that the terms "first" and "second" are merely for the purpose of distinguishing from each other and not for defining a fixed order or a fixed number. The embodiments of the disclosure does not limit the number of the irradiation chambers and the control sub-modules. The first control sub-module may directly or indirectly control the first irradiation chamber to perform the preparatory work, the adjustment during the normal operation, or the like. The embodiment of the present disclosure does not specifically limit the manner in which the first control sub-module controls the first irradiation chamber and the specific control contents. The function of the second control sub-module is similar to that of the first control sub-module, and details are not described herein. The first control sub-module and the second control sub-module in the system control module may include control software and a carrier for executing a control program, or may further include a user input interface and a feedback display interface, or may further include a device connection port of a processor module, a data acquisition module, a beam generation device, a radiation chamber, or the like. The implementation of the first control sub-module and the second control sub-module are not specifically limited in the embodiments of the present disclosure.

In an embodiment of the present disclosure, the beam control module 150 is capable of obtaining data of the beam generation device 130 and connecting to and interacting with the system control module 140. In some embodiments, the beam generation device 130 may transmit data such as beam energy, beam current, water temperature, air pressure, flow rate, beam transmission state, a start time of beam generation, an end time of beam generation, or the like to the beam control module 150, the beam control module 150 transmits the data to the system control module 140, the first control sub-module 141 in the system control module 140 stores various data when the beam generation device 130 emits a beam to the first irradiation chamber 110, and the second control sub-module 142 stores various data when the beam generation device 130 emits a beam to the second irradiation chamber 120. Furthermore, the first control sub-module 141 may transmit data input by a user or historical data of the beam generation device to the beam control module 150 to control the beam generation device 130 to emit a beam to the first irradiation chamber 110, and the second control sub-module 142 may also transmit data input by a user or historical data of the beam generation device to the beam control module 150 to control the beam generation device 130 to emit a beam to the second irradiation chamber 120, thereby achieving data interaction between the beam control module 150 and the system control module 140. The beam generation device 130 may be further connected to and interact with the system control module 140 to directly transmit the above-mentioned data of the beam generation device 130 to the system control module 140 or directly control the beam generation device through the system control module 140. It is to be understood that the data transmitted between the beam control module 150 and the system control module 140 may be the same, or may be different. The embodiments of the present disclosure do not specifically limit whether the data transmitted between the beam control module 150 and the system control module 140 are the same. The specific contents of the data interaction between the beam control module 150 and the system control module 140 may be state data of the beam generation apparatus 130, and may be data of a control instruction sent by a user to the first control sub-module 141 or the second control sub-module 142. The contents of the data interaction between the beam control module 150 and the system control module 140 are not specifically limited in the embodiments of the present disclosure.

In the embodiment of the present disclosure, the beam control module may acquire data from the beam generation device, and the beam control module is connected to the system control module, thereby realizing data interaction between the beam control module and the system control module.

Figure 2:
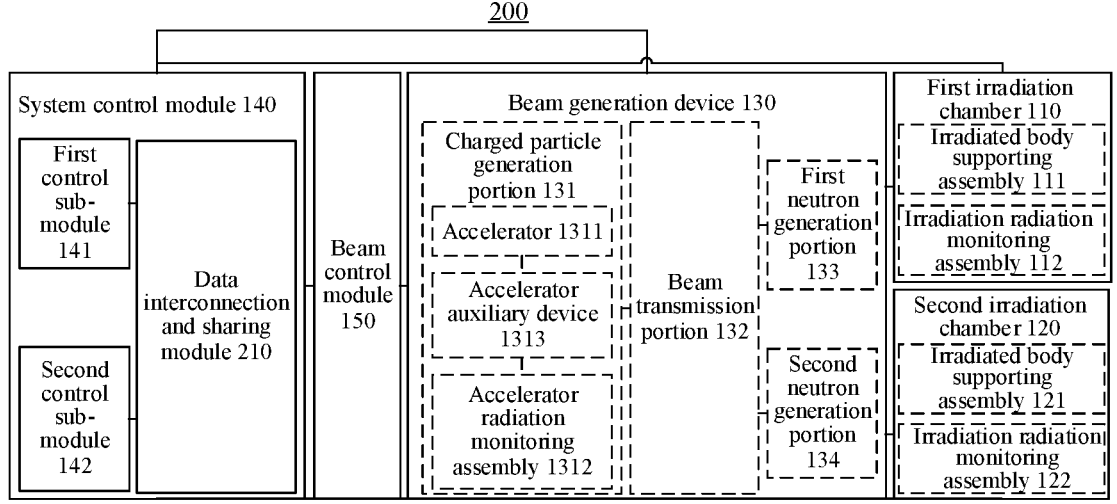
FIG. 2 is a block diagram of a beam irradiation system according to another embodiment of the present disclosure.

FIG. 2 is a block diagram of a beam irradiation system according to another embodiment of the present disclosure. The embodiment shown in FIG. 2 is a modified example of the embodiment shown in FIG. 1. Specifically, a difference from the embodiment shown in FIG. 1 is that the beam irradiation system 200 in the embodiment shown in FIG. 2 further includes a data interconnection and sharing module 210, the first control sub-module 141 and the second control sub-module 142 are connected to and performing data interaction with the data interconnection and sharing module 210 respectively, the first control sub-module 141 and the second control sub-module 142 are further configured to store irradiation data of the first irradiation chamber 110 and the second irradiation chamber 120 respectively, and the data interconnection and sharing module 210 is configured to share the irradiation data of the first irradiation chamber 110 and the second irradiation chamber 120 between the first control sub-module 141 and the second control sub-module 142.

In some embodiments, the beam irradiation system 200 may transmit the irradiation data, such as beam energy, beam current, irradiation time, an ambient radiation value, a switch state of a shielding door, a gamma intensity, a neutron intensity, temperature, humidity, patient data, or a location of a treatment couch, of the first irradiation chamber 110 from the first control sub-module 141 to the second control sub-module 142 through the data interconnect sharing module 210, such that the second control sub-module 142 may treat the irradiated body of the second irradiation chamber 120 more quickly, safely, and accurately, to improve the irradiation effect.

It to be understood that the specific form of the data interconnect sharing module 210 may be pure hardware or may be other forms such as a combination of software and hardware. For example, the device connection port of the processor module, the data acquisition module, the beam generation device, the irradiation chamber or the like is integrated in the data interconnection and sharing module 210, and the collected or received data is transmitted to the first control sub-module and the second control sub-module, and data interaction is performed. Since each hardware interface is integrated in the data interconnection and sharing module, the first control sub-module and the second control sub-module need not to be repeatedly set, and meanwhile, the first control sub-module and the second control sub-module are provided in the form of any control software or in the form of a carrier for performing control, such that the cost of the beam irradiation system may be effectively reduced. It to be understood that a hardware interface may be provided in the first control sub-module and the second control sub-module respectively, and no hardware interface is provided in the data interconnection and sharing module to perform data interaction only. The specific form of the data interconnection and sharing module is not specifically limited in the embodiments of the present disclosure. The irradiation data may be data such as beam energy, beam current, a gamma intensity, a neutron intensity, temperature, humidity, patient data, and a location of a treatment couch, or may be data such as irradiation time, an ambient radiation value, and a switch state of a shielding door. The type of the irradiation data is not specifically limited in the embodiments of the present disclosure. The beam control module 150 may be directly connected to the first control sub-module 141 and the second control sub-module 142, or may be indirectly connected to the first control sub-module 141 and the second control sub-module 142 through the data interconnection and sharing module 210. A manner of connection between the beam control module 150 and the first control sub-module 141 and the second control sub-module 142 is not specifically limited in the embodiments of the present disclosure.

According to the technical solution described in the embodiment of the present disclosure, through providing the data interconnection and sharing module, the data sharing and the state interworking between the first control sub-module and the second control sub-module are realized, which is beneficial to the full utilization of the data. Furthermore, when the data in a control sub-module is difficult to recover, the data is queried and invoked from other control sub-modules through the data interconnection and sharing module, without serious consequences due to data loss.

In one embodiment of the present disclosure, the beam control module 150 is connected to the system control module 140 through the data interconnection and sharing module 210, the beam control module 150 performs data interaction with the data interconnection and sharing module 210, the first irradiation chamber 110 and the second irradiation chamber 120 are connected to and perform data interaction with the data interconnection and sharing module 210, and the first control sub-module 141 and the second control sub-module 142 control the beam control module 150, the first irradiation chamber 110 and the second irradiation chamber 120 through the data interconnection and sharing module 210.

In the embodiment of the disclosure, the beam control module is connected to the system control module through the data interconnection and sharing module, and the beam control module may perform data interaction with the data interconnection and sharing module, such that the beam control module may transmit the data of the beam generation device stored in the beam control module to the data interconnection and sharing module. The data interconnection and sharing module may further transmit the irradiation data of the first irradiation chamber and the second irradiation chamber stored respectively in the first control sub-module and the second control sub-module in the system control module to the beam control module, thereby avoiding resetting various data when other irradiation chambers are required to be used due to a fault of a single control module, and facilitating the user of the beam irradiation system to improve the work efficiency. Furthermore, the first control sub-module and the second control sub-module in the system control module are allowed to control the beam control module, the first irradiation chamber and the second irradiation chamber through the data interconnection and sharing module. In addition, the first irradiation chamber and the second irradiation chamber are configured to be connected to and perform data interaction with the data interconnection and sharing module, data sharing between the first irradiation chamber and the second irradiation chamber is realized, thereby facilitating full utilization of the data between the first irradiation chamber and the second irradiation chamber.

Figure 3:
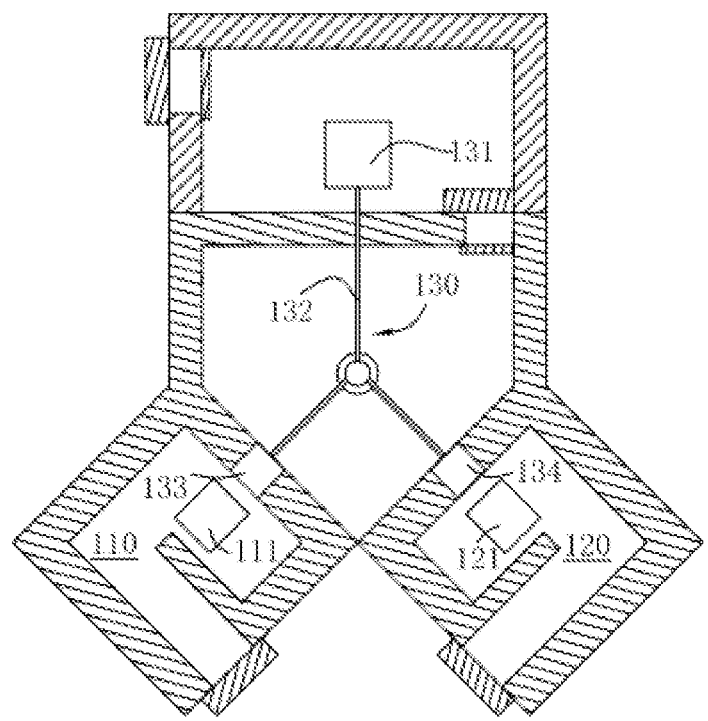
FIG. 3 is a schematic diagram of a device arrangement of a beam irradiation system according to an embodiment of the present disclosure.

Referring to FIG. 3, in an embodiment of the present disclosure, the beam generation apparatus 130 includes a charged particle generation portion 131, a beam transmission portion 132, a first neutron generation portion 133, and a second neutron generation portion 134. The beam control module 150 may control the charged particle generation portion 131 to generate charged particles and may control the beam transmission portion 132 to selectively transmit the charged particles generated by the charged particle generation portion 131 to the first neutron beam generation portion 133 or the second neutron beam generation portion 134. The neutron beam generated by the first neutron beam generation portion 133 is irradiated to the first irradiation chamber 110, and the neutron beam generated by the second neutron beam generation portion 134 is irradiated to the second irradiation chamber 120. The charged particle generation portion 131 is connected to the beam transmission portion 132, and the beam transmission portion 132 is connected to the first neutron generation portion 133 and the second neutron generation portion 134 respectively, to irradiate the neutron beam generated by the first neutron generation portion 133 to the first irradiation chamber 110, or to irradiate the neutron beam generated by the second neutron generation portion 134 to the second irradiation chamber 120.

It is to be understood that the beam generation apparatus 130 includes, but is not limited to, a charged particle generation portion 131, a beam transmission portion 132, a first neutron generation portion 133, and a second neutron generation portion 134. Herein, the first neutron generation portion 133 corresponds to the first irradiation chamber 110, and the second neutron generation portion 134 corresponds to the second irradiation chamber 120. When there is a third irradiation chamber, a third neutron generation portion may be further introduced and corresponds to the third irradiation chamber, and the number of neutron generation portions corresponds to the number of irradiation chambers. The number of neutron generation portions is not specifically limited in the embodiments of the present disclosure. The provision of one charged particle generation portion for transmission to each neutron generation portion effectively reduces the system cost. It to be understood that the beam generation device may further include multiple charged particle generation portions for transmission to the neutron generation portions respectively, and multiple neutron beams may be generated simultaneously in multiple irradiation chambers for irradiation.

In the embodiment of the present disclosure, a charged particle generation portion, a beam transmission portion, a first neutron generation portion, and a second neutron generation portion are provided in the beam generation device, such that a neutron beam is generated to accurately irradiate the first irradiation chamber or the second irradiation chamber. Through providing the beam transmission portion between the charged particle generation portion and the first neutron beam generation portion, or between the charged particle generation portion and the second neutron beam generation portion, the beam transmission portion may selectively transmit the charged particle to the first neutron generation portion or the second neutron generation portion according to a control instruction of the beam control module, such that the first neutron generation portion or the second neutron generation portion generates a neutron beam after being irradiated by the charged particle.

In an embodiment of the present disclosure, the charged particle generation portion 131 includes an accelerator 1311, an accelerator radiation monitoring assembly 1312, and an accelerator auxiliary device 1313, and the beam control module 150 is capable of receiving data information of the accelerator 1311, the accelerator radiation monitoring assembly 1312, and the accelerator auxiliary device 1313 and controlling the accelerator 1311 to generate charged particles.

It is to be understood that the accelerator auxiliary device 1313 may include any auxiliary device for providing a precondition for the operation of the accelerator, and the type of the accelerator auxiliary device 1313 is not specifically limited in the embodiments of the present disclosure. The accelerator radiation monitoring assembly 1312 may include any assembly for monitoring the operation of the accelerator 1311 or the accelerator auxiliary device 1313, and the type of the accelerator auxiliary monitoring assembly 1312 is not specifically limited by embodiments of the present disclosure.

In the embodiment of the present disclosure, through providing the accelerator auxiliary device in the charged particle generation portion, it is convenient to provide the precondition for the normal operation of the accelerator, thereby improving the efficiency and accuracy of the accelerator operation. In addition, through providing the accelerator radiation monitoring assembly, monitoring of the accelerator and the accelerator auxiliary device is realized, such that the personnel is reduced, abnormality of the accelerator auxiliary device may be found in time, and the loss caused by abnormal shutdown of the accelerator, the maintenance time and maintenance cost for the accelerator are reduced.

In an embodiment of the present disclosure, the first irradiation chamber 110 and the second irradiation chamber 120 are provided with the irradiated body supporting assemblies 111, 121 and the irradiation radiation monitoring assemblies 112, 122, respectively, and the system control module 140 is capable of receiving data of the irradiated body supporting assemblies and the irradiation radiation monitoring assemblies and controlling a movement of the irradiated body supporting assemblies.

According to the embodiment of the present disclosure, through arranging the irradiated body supporting member in the first irradiation chamber and the second irradiation chamber, the irradiated body in the first irradiation chamber or the second irradiation chamber may be adjusted conveniently to a proper position, and the irradiated body may be in a comfortable and relaxed state, thereby achieving a better irradiation effect. Through arranging the irradiation radiation monitoring components in the first irradiation chamber and the second irradiation chamber, monitoring of the operating states of the first irradiation chamber and the second irradiation chamber is realized, such that the user may adjust the first irradiation chamber and the second irradiation chamber in time according to the situation occurring in the first irradiation chamber and the second irradiation chamber, thereby improving the working efficiency.

Figure 4:
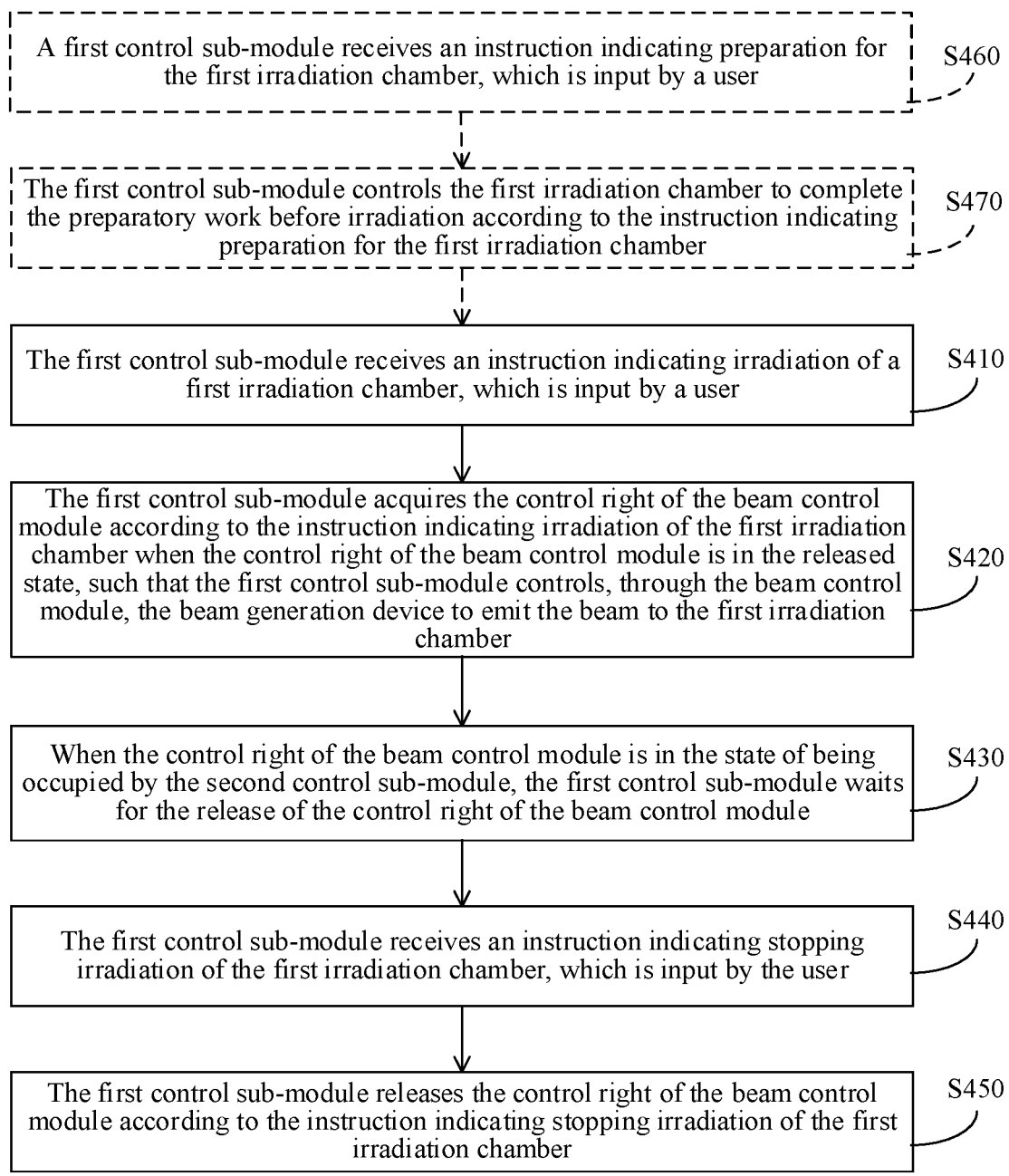
FIG. 4 is a flow chart of a control method for a beam irradiation system according to an embodiment of the present disclosure.

FIG. 4 is a flow chart of a control method for a beam irradiation system according to an embodiment of the present disclosure. As shown in FIG. 4, the control method for the beam irradiation system includes Steps S410 to S450.

In S410, the first control sub-module receives an instruction indicating irradiation of a first irradiation chamber, which is input by a user.

In some embodiments, the user may select to irradiate the first irradiation chamber on the operation interface of the beam irradiation system, i.e., generate an instruction indicating irradiation of a first irradiation chamber. In other embodiments, the user directly inputs an instruction to irradiate the first irradiation chamber on the operation interface of the beam irradiation system, i.e., an instruction indicating irradiation of a first irradiation chamber. According to the embodiment of the disclosure, the generation process of the instruction indicating irradiation of the first irradiation chamber is not specifically limited.

In S420, the first control sub-module acquires the control right of the beam control module according to the instruction indicating irradiation of the first irradiation chamber when the control right of the beam control module is in the released state, such that the first control sub-module controls, through the beam control module, the beam generation device to emit the beam to the first irradiation chamber.

Specifically, when the first control sub-module receives the instruction indicating irradiation of the first irradiation chamber, the first control sub-module queries the control right state of the beam control module. When the first control sub-module finds that the control right of the beam control module is in the released state, the first control sub-module sends an instruction for acquiring the control right of the beam control module to the beam control module. When the beam control module receives the instruction for acquiring the control right of the beam control module, the beam control module hands the control right of the beam control module to the first control sub-module, such that the first control sub-module controls, through the beam control module, the beam generation device to emit the beam to the first irradiation chamber.

In S430, when the control right of the beam control module is in the state of being occupied by the second control sub-module, the first control sub-module waits for the release of the control right of the beam control module.

Specifically, when the first control sub-module receives the instruction indicating irradiation of the first irradiation chamber, the first control sub-module queries the control right state of the beam control module. When the first control sub-module finds that the control right of the beam control module is in the state of being occupied by the second control sub-module, the first control sub-module temporarily fails to acquire the control right of the beam control module. The first control sub-module may query the control right state of the beam control module at intervals of a certain time until the query result is that the control right of the beam control module is in the released state.

In S440, the first control sub-module receives an instruction indicating stopping irradiation of the first irradiation chamber, which is input by the user.

In some embodiments, the user may generate an instruction indicating stopping irradiation of the first irradiation chamber by clicking an option of stopping the first irradiation chamber irradiation on an operation interface of the beam irradiation system. In other embodiments, the user may directly enter an instruction to stop the first irradiation chamber irradiation, i.e., an instruction indicating stopping irradiation of the first irradiation chamber. In other embodiments, the first control sub-module may further automatically generate the instruction indicating stopping irradiation of the first irradiation chamber when it is detected that the irradiated body is offset to the target position, or when the operation on the irradiation chamber is completed or the like. According to the embodiment of the disclosure, the generation of the instruction indicating stopping irradiation of the first irradiation chamber is not specifically limited.

In S450, the first control sub-module releases the control right of the beam control module according to the instruction indicating stopping irradiation of the first irradiation chamber.

Specifically, the first control sub-module stops the control of the beam control module according to the instruction indicating stopping irradiation of the first irradiation chamber, and when the beam control module stops working, the first control sub-module completely releases the control right of the beam control module.

According to the technical solution provided in the embodiment of the present disclosure, any one of the multiple control sub-modules such as the first control sub-module or the second control sub-module, controls, through the beam control module, the beam generation device to emit a beam to the corresponding irradiation chamber, such that the first control sub-module controls the first irradiation chamber and the second control sub-module controls the second irradiation chamber in the system control module. When the first control sub-module is in an overhaul state or when a software or hardware damage occurs, the second control sub-module may be used to control the second irradiation chamber, thereby overcoming the difficulty of irradiation when a single control module is in the overhaul state or when a software or hardware damage occurs, which would affect the normal operation. In addition, one beam control module is jointly controlled by multiple control sub-modules such as the first control sub-module and the second control sub-module, thereby reducing the cost of the beam irradiation system.

In an embodiment of the present disclosure, the control method further includes steps S460 and S470 before the first control sub-module receives the instruction indicating irradiation of the first irradiation chamber, which is input by the user or when the control right of the beam control module is in the state of being occupied by the second control sub-module.

In S460, the first control sub-module receives an instruction indicating preparation for the first irradiation chamber, which is input by a user.

In some embodiments, the user may select to allow the first irradiation chamber to enter the preparatory work on the operation interface of the beam irradiation system, i.e., generate an instruction indicating preparation for the first irradiation chamber. In other embodiments, the user directly inputs an instruction to allow the first irradiation chamber to enter the preparatory work on the operation interface of the beam irradiation system, i.e., an instruction indicating preparation for the first irradiation chamber. According to the embodiment of the disclosure, the generation of the instruction indicating preparation for the first irradiation chamber is not specifically limited. The instruction indicating preparation for the first irradiation chamber may include an instruction to place a couch or locate an irradiated body, and the type of the instruction indicating preparation for the first irradiation chamber is not specifically limited in the embodiments of the present disclosure.

In S470, the first control sub-module controls the first irradiation chamber to complete the preparatory work before irradiation according to the instruction indicating preparation for the first irradiation chamber.

The first control sub-module may be directly connected to the first irradiation chamber so as to control the first irradiation chamber to complete the preparatory work before irradiation according to the instruction indicating preparation for the first irradiation chamber, and the first control sub-module may be indirectly connected to the first irradiation chamber so as to control the first irradiation chamber to complete the preparatory work before irradiation according to the instruction indicating preparation for the first irradiation chamber. The embodiment of the present disclosure does not specifically limit the manner in which the first control sub-module is directly or indirectly connected to the first irradiation chamber. The preparatory work may include placing the couch or locating the irradiated body, or the like, and the contents of the preparatory work are not specifically limited in the embodiments of the present disclosure.

In the embodiment of the present disclosure, before the first control sub-module receives the instruction indicating irradiation of the first irradiation chamber, which is input by the user or when the control right of the beam control module is in the state of being occupied by the second control sub-module, the first control sub-module controls the first irradiation chamber to complete the preparatory work before irradiation according to the received instruction indicating preparation for the first irradiation chamber, which is input by the user, such that the preparatory work is completed before the first irradiation chamber is irradiated, thereby improving the usage rate of the beam irradiation system and the working efficiency of the user operating the beam irradiation system.

Figure 5:
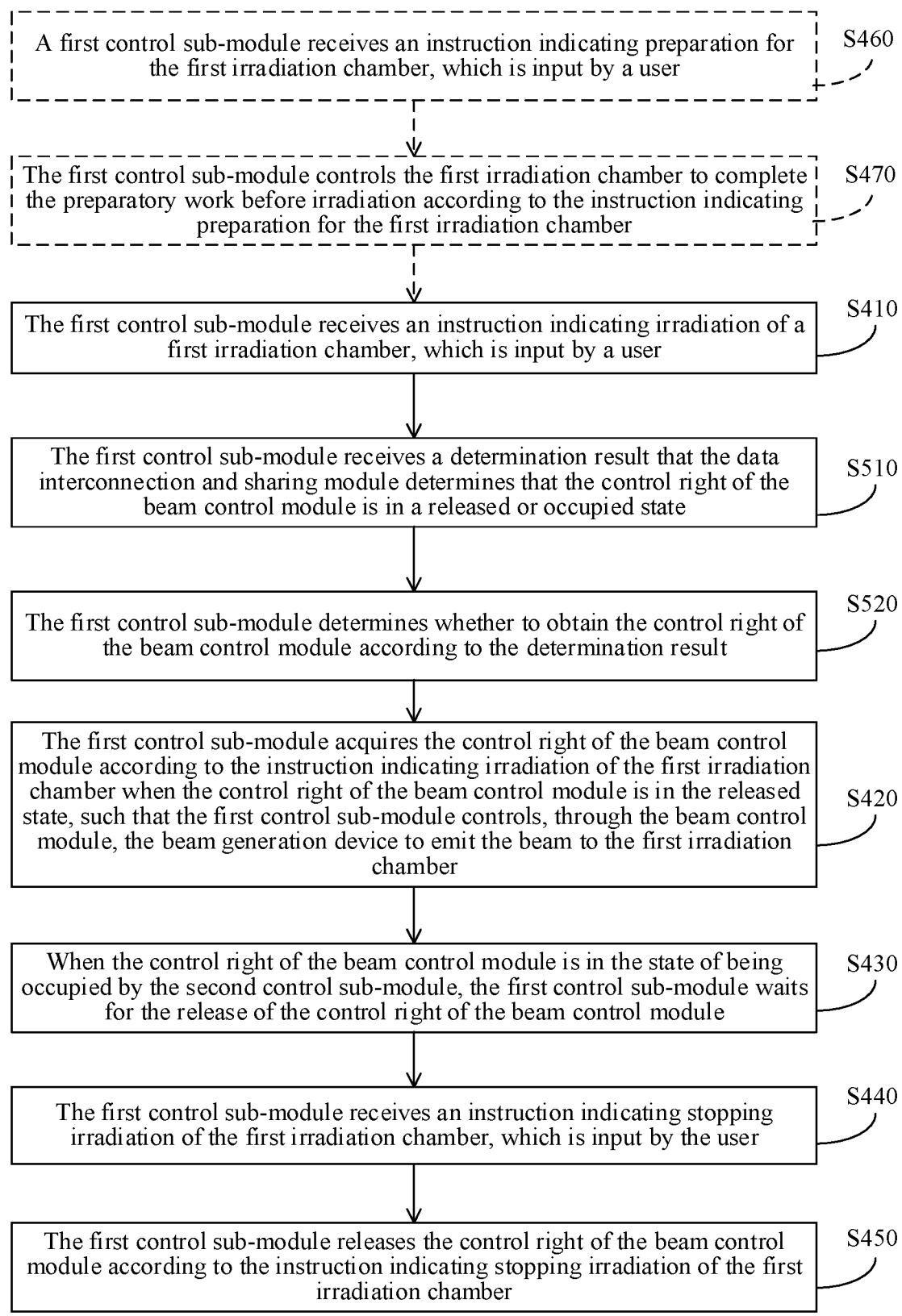
FIG. 5 is a flow chart of a control method for a beam irradiation system according to another embodiment of the present disclosure.

FIG. 5 is a flow chart of a control method for a beam irradiation system according to another embodiment of the present disclosure. The system control module further includes a data interconnection and sharing module. Here, the data interconnection and sharing module is connected to the first control sub-module and the second control sub-module, the first control sub-module and the second control sub-module are connected to the beam control module respectively, and the control method further includes Steps S510 and S520.

In S510, the first control sub-module receives a determination result that the data interconnection and sharing module determines that the control right of the beam control module is in a released or occupied state.

Specifically, the data interconnection and sharing module determines whether the control right of the beam control module is in the released state or in the occupied state. The data interconnection and sharing module sends a determination result of determining whether the control right of the beam control module is in the released or occupied state to the first control sub-module, and the first control sub-module receives the determination result.

In S520, the first control sub-module determines whether to obtain the control right of the beam control module according to the determination result.

Specifically, when the determination result is that the control right of the beam control module is in the released state, the first control sub-module determines, based on the determination result, that the control right of the beam control module can be obtained; and when the determination result is that the control right of the beam control module is in the occupied state, the first control sub-module determines, according to the determination result, that the control right of the beam control module cannot be obtained.

According to the technical solution provided in the embodiment of the present disclosure, the first control sub-module receives a determination result that the data interconnection and sharing module determines that the control right of the beam control module is in a released or occupied state, and the first control sub-module determines whether to obtain the control right of the beam control module according to the determination result, thereby realizing accurate determination of the control right of the beam control module through the data interconnection and sharing module, and facilitating the first control sub-module to obtain the control right of the beam control module.

Figure 6:
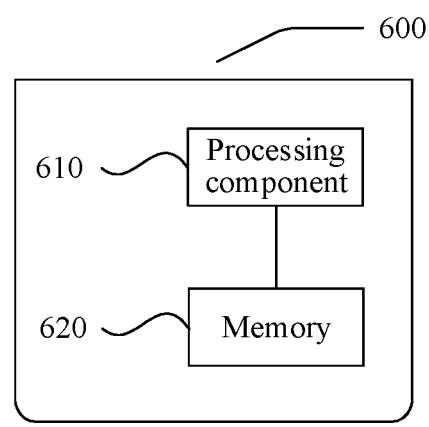
FIG. 6 is a block diagram of a control system for a beam irradiation system according to an embodiment of the present disclosure.

FIG. 6 is a block diagram of a control system 600 of a beam irradiation system according to an embodiment of the present disclosure.

Referring to FIG. 6, the control system 600 includes a processing component 610. The processing component 610 further includes one or more processors, and memory resources represented by memory 620, for storing instructions executable by the processing component 610, such as applications. The applications stored in memory 620 may include one or more modules each corresponding to a set of instructions. Further, the processing component 610 is configured to execute the instructions to perform the control methods for the beam irradiation system described above.

The control system 600 may further include a power supply component configured to perform power management of the control system 600, a wired or wireless network interface configured to connect the control system 600 to a network, and an input/output (I/O) interface. The control system 600 may operate based on an operating system stored in memory 620, such as Windows Server™, Mac OS X™, Unix™, Linux™, FreeBSD™, or the like.

A non-transitory computer readable storage medium is provided. When the instructions in the storage medium are executed by a processor of the control system 600, the storage medium enables the control system 600 to perform a control method for a beam irradiation system. In the method, a first control sub-module receives an instruction indicating irradiation of a first irradiation chamber, which is input by a user; the first control sub-module obtains the control right of the beam control module according to the instruction indicating irradiation of the first irradiation chamber, and when the control right of the beam control module is in the released state, the first control sub-module controls the beam generation device to emit a beam to the first irradiation chamber through the beam control module, and when the control right of the beam control module is in the state of being occupied by the second control sub-module, the first control sub-module waits for the control right of the beam control module to be released; the first control sub-module receives an instruction indicating stopping irradiation of the first irradiation chamber, which is input by the user; and the first control sub-module releases the control right of the beam control module according to the instruction indicating stopping irradiation of the first irradiation chamber.

Those of ordinary skill in the art will recognize that the modules and method steps of the various examples described in connection with the embodiments disclosed herein may be implemented in electronic hardware, or a combination of computer software and electronic hardware. Whether these functions are performed in hardware or software depends on the particular application and design constraints of the solution. The skilled person may use different methods to implement the described functions for each particular application, but such implementation should not be considered to be beyond the scope of the present disclosure.

It will be apparent to those skilled in the art that for the convenience and brevity of the description, reference may be made to the beam irradiation system in the foregoing embodiments for the specific operation of the above-described methods, and no further description will be given herein.

In the several embodiments provided herein, it to be understood that the disclosed beam irradiation system and the control method thereof may be implemented in other ways. For example, the beam irradiation system embodiment described above is merely illustrative. For example, the partitioning of the module is only partitioning of logical functions, and may be implemented in another partitioning manner. For example, multiple modules or components may be combined or integrated into another system, or some features may be ignored or not performed. Alternatively, the illustrated or discussed coupling or direct coupling or communication connection to each other may be through some interface, and the indirect coupling or communication connection of modules or components may be electrical, mechanical or other.

The modules illustrated as separate components may or may not be physically separate, and the components shown as modules may or may not be physical units, may be located in one location, or may be distributed across multiple network units. Some or all of the elements may be selected according to actual needs to achieve the objectives of the embodiments.

The functions, when implemented as software functional units and sold or used as separate products, may be stored in a computer-readable storage medium. On the basis of such an understanding, the technical solution of the present disclosure may essentially be embodied in the form of a software product, which is stored in a storage medium and includes instructions for causing a computer device (which may be a personal computer, a server, a network device, or the like) to perform all or part of the steps of the methods described in the various embodiments of the present disclosure. The storage medium includes a USB flash drive, a removable hard disk, a read-only memory (ROM), a random access memory (RAM), a magnetic disk, or an optical disk.

It is further to be noted that the combination of the technical features in the present disclosure is not limited to the combination described in the claims in the present disclosure or the combination described in the specific embodiments, and all the technical features described in the present disclosure may be freely combined or combined in any manner unless there is a contradiction between them.

Although the illustrative embodiments of the present invention have been described above in order to enable those skilled in the art to understand the present invention, it should be understood that the present invention is not to be limited the scope of the embodiments. For those skilled in the art, as long as various changes are within the spirit and scope as defined in the present invention and the appended claims, these changes are obvious and within the scope of protection claimed by the present invention.

What is claimed is:

1. A beam irradiation system, comprising:
   two irradiation chambers, comprising a first irradiation chamber and a second irradiation chamber;
   a beam generation device configured to generate a beam and emit the beam to the first irradiation chamber or the second irradiation chamber;
   a system control module including two control sub-modules one-to-one corresponding to the two irradiation chambers, the two control sub-modules including a first control sub-module and a second control sub-module, wherein the first control sub-module corresponds to the first irradiation chamber and is capable of controlling the beam generation device to emit the beam to the first irradiation chamber, and the second control sub-module corresponds to the second irradiation chamber and is capable of controlling the beam generation device to emit the beam to the second irradiation chamber; and
   a beam control module connected between the beam generation device and the system control module, one of the first control sub-module and the second control sub-module being capable of controlling the beam generation device through the beam control module when the beam control module is not occupied by the other of the first control sub-module and the second control sub-module.

2. The beam irradiation system according to claim 1, wherein the beam control module is capable of obtaining data of the beam generation device and performing data interaction with the system control module, and the beam generation device is connected to and performs data interaction with the system control module.

3. The beam irradiation system according to claim 1, wherein the first irradiation chamber and the second irradiation chamber are provided with an irradiated body supporting assembly and an irradiation radiation monitoring assembly, and the system control module is capable of receiving data of the irradiated body supporting assembly and the irradiation radiation monitoring assembly and controlling a movement of the irradiated body supporting assembly.

4. The beam irradiation system according to claim 1, wherein the system control module further comprises a data interconnection and sharing module, the first control sub-module and the second control sub-module are respectively connected to and perform data interaction with the data interconnection and sharing module, the first control sub-module and the second control sub-module are further configured to store irradiation data of the first irradiation chamber and the second irradiation chamber, respectively, and the data interconnection and sharing module is configured to share the irradiation data of the first irradiation chamber and the second irradiation chamber between the first control sub-module and the second control sub-module.

5. The beam irradiation system according to claim 4, wherein the beam control module is connected to the system control module through the data interconnection and sharing module, the beam control module performs data interaction with the data interconnection and sharing module, the first irradiation chamber and the second irradiation chamber are connected to and perform data interaction with the data interconnection and sharing module, and the first control sub-module and the second control sub-module control the beam control module, the first irradiation chamber and the second irradiation chamber through the data interconnection and sharing module.

6. The beam irradiation system according to claim 1, wherein the beam generation device comprises a charged particle generation portion, a beam transmission portion, a first neutron generation portion and a second neutron generation portion, the beam control module being capable of controlling the charged particle generation portion to generate charged particles and capable of controlling the beam transmission portion to selectively transmit the charged particles generated by the charged particle generation portion to the first neutron beam generation portion or the second neutron beam generation portion, a neutron beam generated by the first neutron beam generation portion being irradiated to the first irradiation chamber, and a neutron beam generated by the second neutron beam generation portion being irradiated to the second irradiation chamber.

7. The beam irradiation system according to claim 6, wherein the charged particle generation portion comprises an accelerator, an accelerator radiation monitoring assembly and an accelerator auxiliary device, the beam control module being capable of receiving data information of the accelerator, the accelerator radiation monitoring assembly and the accelerator auxiliary device and controlling the accelerator to generate charged particles.

8. A control method for the beam irradiation system according to claim 1, comprising:
receiving, by the first control sub-module, an instruction indicating irradiation of the first irradiation chamber, which is input by a user;
obtaining, by the first control sub-module, a control right of the beam control module according to the instruction indicating irradiation of the first irradiation chamber when the control right of the beam control module is in a released state, so as to control, through the beam control module, the beam generation device to emit a beam to the first irradiation chamber;
waiting, by the first control sub-module, for a release of the control right of the beam control module, when the control right of the beam control module is in a state of being occupied by the second control sub-module;
receiving, by the first control sub-module, an instruction indicating stopping irradiation of the first irradiation chamber, which is input by the user; and
releasing, by the first control sub-module, the control right of the beam control module according to the instruction indicating stopping irradiation of the first irradiation chamber.

9. The control method according to claim 8, wherein before receiving, by the first control sub-module, the instruction indicating irradiation of the first irradiation chamber, which is input by the user, or when the control right of the beam control module is in the state of being occupied by the second control sub-module, the control method further comprises:
receiving, by the first control sub-module, an instruction indicating preparation for the first irradiation chamber, which is input by the user; and
controlling, by the first control sub-module, the first irradiation chamber to complete a preparatory work before irradiation according to the instruction indicating preparation for the first irradiation chamber.

10. The control method according to claim 8, wherein the system control module further comprises a data interconnection and sharing module, wherein the data interconnection and sharing module is connected to the first control sub-module and the second control sub-module, and the first control sub-module and the second control sub-module are connected to the beam control module through the data interconnection and sharing module, respectively, and the control method further comprises:
receiving, by the first control sub-module, a determination result of determining, by the data interconnection and sharing module, that the control right of the beam control module is in a released state or an occupied state; and
determining, by the first control sub-module according to the determination result, whether the control right of the beam control module is to be obtained.

11. A beam irradiation system, comprising:
two irradiation chambers, comprising a first irradiation chamber and a second irradiation chamber;
a beam generation device configured to generate a beam and emit the beam to the first irradiation chamber or the second irradiation chamber; and
a system control module including two control sub-modules one-to-one corresponding to the two irradiation chambers, the two control sub-modules including a first control sub-module, a second control sub-module and a data interconnection and sharing module, wherein the first control sub-module corresponds to the first irradiation chamber and is capable of controlling the beam generation device to emit the beam to the first irradiation chamber, the second control sub-module corresponds to the second irradiation chamber and is capable of controlling the beam generation device to emit the beam to the second irradiation chamber, the first control sub-module and the second control sub-module are connected to and perform data interaction with the data interconnection and sharing module respectively.

12. The beam irradiation system according to claim 11, wherein the first control sub-module and the second control sub-module are configured to store irradiation data of the first irradiation chamber and the second irradiation chamber, respectively, and the data interconnection and sharing module is configured to share the irradiation data of the first irradiation chamber and the second irradiation chamber between the first control sub-module and the second control sub-module.

13. The beam irradiation system according to claim 11, wherein the first irradiation chamber and the second irradiation chamber are provided with an irradiated body supporting assembly and an irradiation radiation monitoring assembly, and the system control module is capable of receiving data of the irradiated body supporting assembly and the irradiation radiation monitoring assembly and controlling a movement of the irradiated body supporting assembly.

14. The beam irradiation system according to claim 11, further comprising a beam control module connected between the beam generation device and the system control module, the beam control module is capable of obtaining data of the beam generation device and performs data interaction with the system control module, wherein the beam generation device is connected to and performs data interaction with the system control module.

15. The beam irradiation system according to claim 14, wherein one of the first control sub-module and the second control sub-module being capable of controlling the beam generation device through the beam control module when the beam control module is not occupied by the other of the first control sub-module and the second control sub-module.

16. The beam irradiation system according to claim 14, wherein the beam control module is connected to the system control module through the data interconnection and sharing module; the beam control module performs data interaction with the data interconnection and sharing module; the first irradiation chamber, the second irradiation chamber are connected to and perform data interaction with the data interconnection and sharing module respectively; and the first control sub-module and the second control sub-module control the beam control module, the first irradiation chamber and the second irradiation chamber through the data interconnection and sharing module.

17. The beam irradiation system according to claim 14, wherein the beam generation device comprises a charged particle generation portion, a beam transmission portion, a first neutron generation portion and a second neutron generation portion, the beam control module being capable of controlling the charged particle generation portion to generate charged particles and capable of controlling the beam transmission portion to selectively transmit the charged particles generated by the charged particle generation portion to the first neutron beam generation portion or the second neutron beam generation portion, a neutron beam generated by the first neutron beam generation portion being irradiated to the first irradiation chamber, and a neutron beam generated by the second neutron beam generation portion being irradiated to the second irradiation chamber.

18. The beam irradiation system according to claim 17, wherein the charged particle generation portion comprises an accelerator, an accelerator radiation monitoring assembly and an accelerator auxiliary device, the beam control module being capable of receiving data information of the accelerator, the accelerator radiation monitoring assembly and the accelerator auxiliary device and controlling the accelerator to generate charged particles.

* * * * *